US010939971B2

(12) United States Patent
Griffiths

(10) Patent No.: US 10,939,971 B2
(45) Date of Patent: Mar. 9, 2021

(54) SYSTEM AND METHOD FOR PROVIDING FEEDBACK DURING MANUAL JOINT POSITIONING

(71) Applicant: INTUITIVE SURGICAL OPERATIONS, INC., Sunnyvale, CA (US)

(72) Inventor: Paul G. Griffiths, Santa Clara, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

(21) Appl. No.: 16/934,774

(22) Filed: Jul. 21, 2020

(65) Prior Publication Data

US 2020/0345434 A1 Nov. 5, 2020

Related U.S. Application Data

(63) Continuation of application No. 15/558,525, filed as application No. PCT/US2016/022553 on Mar. 16, 2016, now Pat. No. 10,751,135.

(Continued)

(51) Int. Cl.
 *B25J 9/16* (2006.01)
 *A61B 34/30* (2016.01)
 (Continued)

(52) U.S. Cl.
 CPC .............. *A61B 34/30* (2016.02); *A61B 34/76* (2016.02); *A61B 34/77* (2016.02); *B25J 1/02* (2013.01);
 (Continued)

(58) Field of Classification Search
 USPC .................................................. 700/245–264
 See application file for complete search history.

(56) References Cited

U.S. PATENT DOCUMENTS 6,441,577 B2 * 8/2002 Blumenkranz ........ B25J 9/1689
 128/DIG. 7
9,737,371 B2 * 8/2017 Romo .................... A61B 34/32
 (Continued)

FOREIGN PATENT DOCUMENTS

CN 101031236 A 9/2007
CN 101448467 A 6/2009
 (Continued)

OTHER PUBLICATIONS

Extended European Search Report for Application No. EP16765614. 9, dated Oct. 5, 2018, 10 pages.
 (Continued)

*Primary Examiner* — Jonathan L Sample
(74) *Attorney, Agent, or Firm* — Artegis Law Group, LLP

(57) ABSTRACT

A system and method of providing feedback during manual joint positioning includes a computer-assisted device having an articulated structure including a joint and a control unit coupled to the articulated structure. To provide feedback to a user during manual positioning of the joint by a user, the control unit is configured to determine a first target position for the joint, release a brake associated with the joint when the joint is moving toward the first target position, apply the brake when the joint is moving away from the first target position, and change the first target position to a second target position when the joint is at the first target position.

20 Claims, 4 Drawing Sheets

Related U.S. Application Data

(60) Provisional application No. 62/134,193, filed on Mar. 17, 2015.

(51) Int. Cl.

| | | |
|---|---|---|
| *B25J 13/02* | (2006.01) | |
| *B25J 19/00* | (2006.01) | |
| *A61B 34/00* | (2016.01) | |
| *B25J 3/04* | (2006.01) | |
| *B25J 1/02* | (2006.01) | |
| B25J 9/06 | (2006.01) | |
| A61B 90/50 | (2016.01) | |
| A61B 34/35 | (2016.01) | |
| A61B 34/37 | (2016.01) | |

(52) U.S. Cl.
CPC .............. *B25J 3/04* (2013.01); *B25J 9/1689* (2013.01); *B25J 13/025* (2013.01); *B25J 19/0004* (2013.01); *A61B 34/35* (2016.02); *A61B 34/37* (2016.02); *A61B 2090/508* (2016.02); *B25J 9/06* (2013.01)

(56) References Cited

U.S. PATENT DOCUMENTS

| | | | |
|---|---|---|---|
| 10,751,135 B2 | 8/2020 | Griffiths | |
| 2006/0142657 A1* | 6/2006 | Quaid | A61B 17/1764 600/424 |
| 2007/0021738 A1* | 1/2007 | Hasser | A61B 90/361 606/1 |
| 2007/0151389 A1* | 7/2007 | Prisco | A61B 34/70 74/490.05 |
| 2009/0024142 A1* | 1/2009 | Ruiz Morales | A61B 34/35 606/130 |
| 2009/0036902 A1* | 2/2009 | DiMaio | A61B 34/37 606/130 |
| 2010/0204713 A1* | 8/2010 | Ruiz Morales | A61B 34/37 606/130 |
| 2011/0082587 A1* | 4/2011 | Ziaei | A61B 17/162 700/260 |
| 2011/0282491 A1* | 11/2011 | Prisco | A61B 34/30 700/258 |
| 2012/0123441 A1* | 5/2012 | Au | A61B 34/30 606/130 |
| 2014/0052153 A1* | 2/2014 | Griffiths | A61B 34/30 606/130 |
| 2014/0052154 A1* | 2/2014 | Griffiths | A61B 90/50 606/130 |
| 2014/0276952 A1* | 9/2014 | Hourtash | A61B 34/30 606/130 |
| 2016/0113728 A1* | 4/2016 | Piron | A61B 34/20 606/130 |
| 2017/0079731 A1* | 3/2017 | Griffiths | B25J 9/02 |
| 2018/0078320 A1* | 3/2018 | Griffiths | A61B 34/76 |

FOREIGN PATENT DOCUMENTS

| | | |
|---|---|---|
| WO | WO-2011109041 A1 | 9/2011 |
| WO | WO-2014139023 A1 | 9/2014 |

OTHER PUBLICATIONS

International Search Report and Written Opinion for Application No. PCT/US2016/022553, dated Jun. 13, 2016, 11 pages.

Nef T., et al., "ARMin—Robot for Rehabilitation of the Upper Extremities," Proceedings of the 2006 IEEE International Conference on Robotics and Automation, May 2006, pp. 3152-3157.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEM AND METHOD FOR PROVIDING FEEDBACK DURING MANUAL JOINT POSITIONING

RELATED APPLICATIONS

This patent application is a continuation of U.S. patent application Ser. No. 15/558,525, filed on Sep. 14, 2017, which is a U.S. National Stage patent application of International Patent Application No. PCT/US2016/022553, filed on Mar. 16, 2016, the benefit of which is claimed, and claims priority to and the benefit of the filing date of U.S. Provisional Patent Application No. 62/134,193, entitled "System and method for providing feedback during manual joint positioning", filed Mar. 17, 2015, each of which is incorporated by reference herein in its entirety.

TECHNICAL FIELD

The present disclosure relates generally to operation of devices with articulated arms and more particularly to providing feedback during manual joint positioning.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices.

These electronic devices provide both advantages and challenges to the personnel operating them. Many of these electronic devices may be capable of autonomous or semi-autonomous motion of one or more articulated arms and/or end effectors. These one or more articulated arms and/or end effectors each include a combination of links and articulated joints that support motion of the articulated arms and/or end effectors. In many cases, the articulated joints are manipulated to obtain a desired position and/or orientation (collectively, a desired pose) of a corresponding tool located at a distal end of the links and articulated joints of a corresponding articulated arm and/or end effector. Each of the articulated joints proximal to the tool provides the corresponding articulated arm and/or end effector with at least one degree of freedom that may be used to manipulate the position and/or orientation of the corresponding tool. In many cases, the corresponding articulated arms and/or end effectors may include at least six degrees of freedom that allow for controlling a x, y, and z position of the corresponding tool as well as a roll, pitch, and yaw orientation of the corresponding tool.

In some cases, an operator may desire to guide an articulated arm into a particular configuration (i.e., to manually position one or more joints in the arm). However, with so many degrees of freedom, an operator may experience difficulty determining when the desired configuration has been obtained. The operator may further experience difficulty deciding which direction to move the joints to reach the desired configuration. Still further, the operator may be unaware of physical and/or practical constraints associated with each joint such as a maximum allowable joint velocity, range of motion limits, and/or the like. As a result, an operator attempting to manually position one or more joints of an articulated arm to reach a predetermined configuration may struggle to do so accurately, quickly, and/or without risking damage to the device and/or injury to nearby personnel such as the operator and/or a patient.

Accordingly, it would be desirable to provide feedback to the operator to facilitate manual joint positioning.

SUMMARY

Consistent with some embodiments, a computer-assisted medical device includes an articulated arm comprising a joint and a control unit coupled to the articulated arm. The control unit is configured to provide feedback during manual positioning of the joint by determining a target position for the join, determining kinematics of the joint relative to the target position, and providing feedback based on the kinematics of the joint.

Consistent with some embodiments, a method of providing feedback during manual positioning of a joint of a computer-assisted medical device includes determining a target position for the joint, determining kinematics of the joint relative to the target position, and providing feedback based on the kinematics of the joint.

Consistent with some embodiments, a non-transitory machine-readable medium includes a plurality of machine-readable instructions which when executed by one or more processors associated with a medical device are adapted to cause the one or more processors to perform a method. The method includes determining a target position for a joint during manual positioning of the joint, determining kinematics of the joint relative to the target position, and providing feedback based on the kinematics of the joint.

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and spirit of this disclosure. In addition, to avoid unnecessary repetition, one or more features shown and described in association with one embodiment may be incorporated into other embodiments unless specifically described otherwise or if the one or more features would make an embodiment non-functional.

Figure 1:
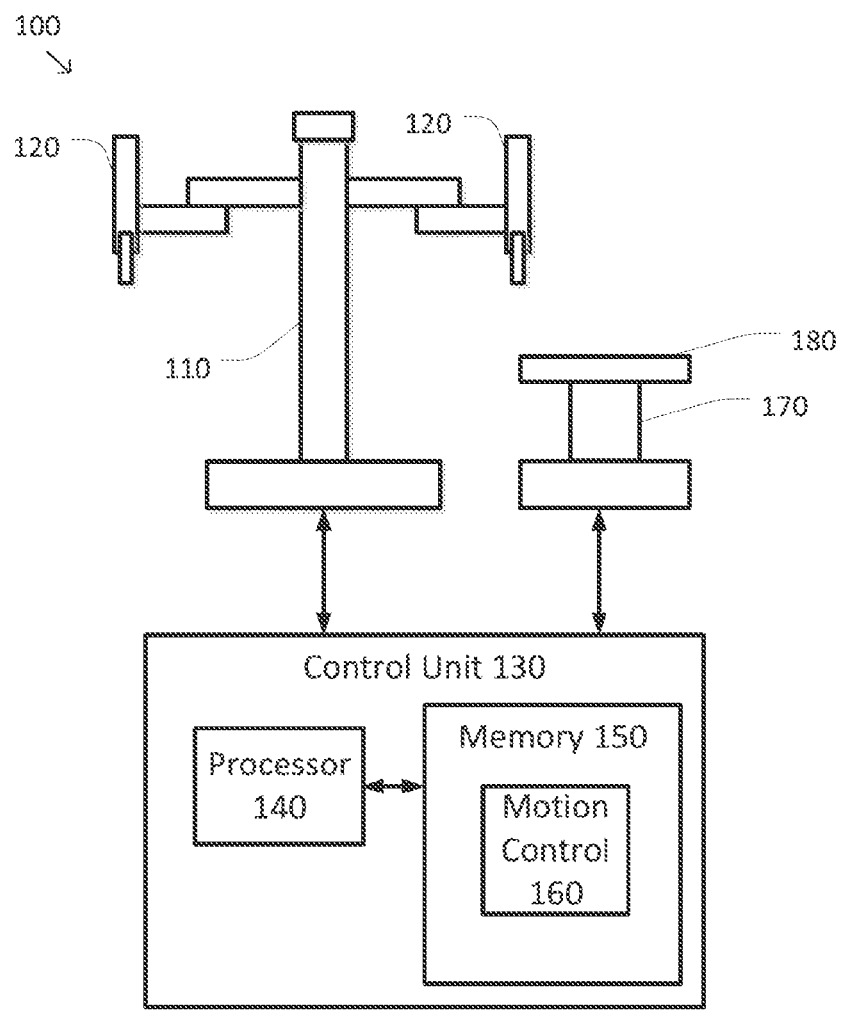
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a device 110 with one or more movable or articulated arms 120. Each of the one or more articulated arms 120 may support one or more end effectors. In some examples, device 110 may be consistent with a computer-assisted surgical device. The one or more articulated arms 120 may each provide support for one or more tools, surgical instruments, imaging devices, and/or the like mounted to a distal end of at least one of the articulated arms 120. Device 110 may further be coupled to an operator workstation (not shown), which may include one or more master controls for operating the device 110, the one or more articulated arms 120, and/or the end effectors. In some embodiments, device 110 and the operator workstation may correspond to a da Vinci® Surgical System commercialized by Intuitive Surgical, Inc. of Sunnyvale, Calif. In some embodiments, computer-assisted surgical devices with other configurations, fewer or more articulated arms, and/or the like may be used with computer-assisted system 100.

Device 110 is coupled to a control unit 130 via an interface. The interface may include one or more wireless links, cables, connectors, and/or buses and may further include one or more networks with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), and/or the like in control unit 130. Control unit 130 may be implemented as a stand-alone subsystem and/or board added to a computing device or as a virtual machine. In some embodiments, control unit may be included as part of the operator workstation and/or operated separately from, but in coordination with the operator workstation.

Memory 150 may be used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 150 includes a motion control application 160 that may be used to support autonomous and/or semiautonomous control of device 110. Motion control application 160 may include one or more application programming interfaces (APIs) for receiving position, motion, and/or other sensor information from device 110, exchanging position, motion, and/or collision avoidance information with other control units regarding other devices, such as a surgical table and/or imaging device, and/or planning and/or assisting in the planning of motion for device 110, articulated arms 120, and/or the end effectors of device 110. And although motion control application 160 is depicted as a software application, motion control application 160 may be implemented using hardware, software, and/or a combination of hardware and software.

In some embodiments, computer-assisted system 100 may be found in an operating room and/or an interventional suite. And although computer-assisted system 100 includes only one device 110 with two articulated arms 120, one of ordinary skill would understand that computer-assisted system 100 may include any number of devices with articulated arms and/or end effectors of similar and/or different design from device 110. In some examples, each of the devices may include fewer or more articulated arms and/or end effectors.

Computer-assisted system 100 further includes a surgical table 170. Like the one or more articulated arms 120, surgical table 170 may support articulated movement of a table top 180 relative to a base of surgical table 170. In some examples, the articulated movement of table top 180 may include support for changing a height, a tilt, a slide, a Trendelenburg orientation, and/or the like of table top 180. Although not shown, surgical table 170 may include one or more control inputs, such as a control pendant for controlling the position and/or orientation of table top 180. In some embodiments, surgical table 170 may correspond to one or more of the operating tables commercialized by Trumpf Medical Systems GmbH of Germany.

Surgical table 170 may also be coupled to control unit 130 via a corresponding interface. The interface may include one or more wireless links, cables, connectors, and/or buses and may further include one or more networks with one or more network switching and/or routing devices. In some embodiments, surgical table 170 may be coupled to a different control unit than control unit 130. In some examples, motion control application 160 may include one or more application programming interfaces (APIs) for receiving position, motion, and/or other sensor information associated with surgical table 170 and/or table top 180. In some examples, motion control application 160 may plan and/or assist in the planning of motion for surgical table 170 and/or table top 180. In some examples, motion control application 160 may prevent motion of surgical table 170 and/or table top 180, such as by preventing movement of surgical table 170 and/or table top 180 through use of the control pendant. In some examples, motion control application 160 may help register device 110 with surgical table 170 so that a geometric relationship between device 110 and surgical table 170 is known. In some examples, the geometric relationship may include a translation and/or one or more rotations between coordinate frames maintained for device 110 and surgical table 170.

Figure 2:
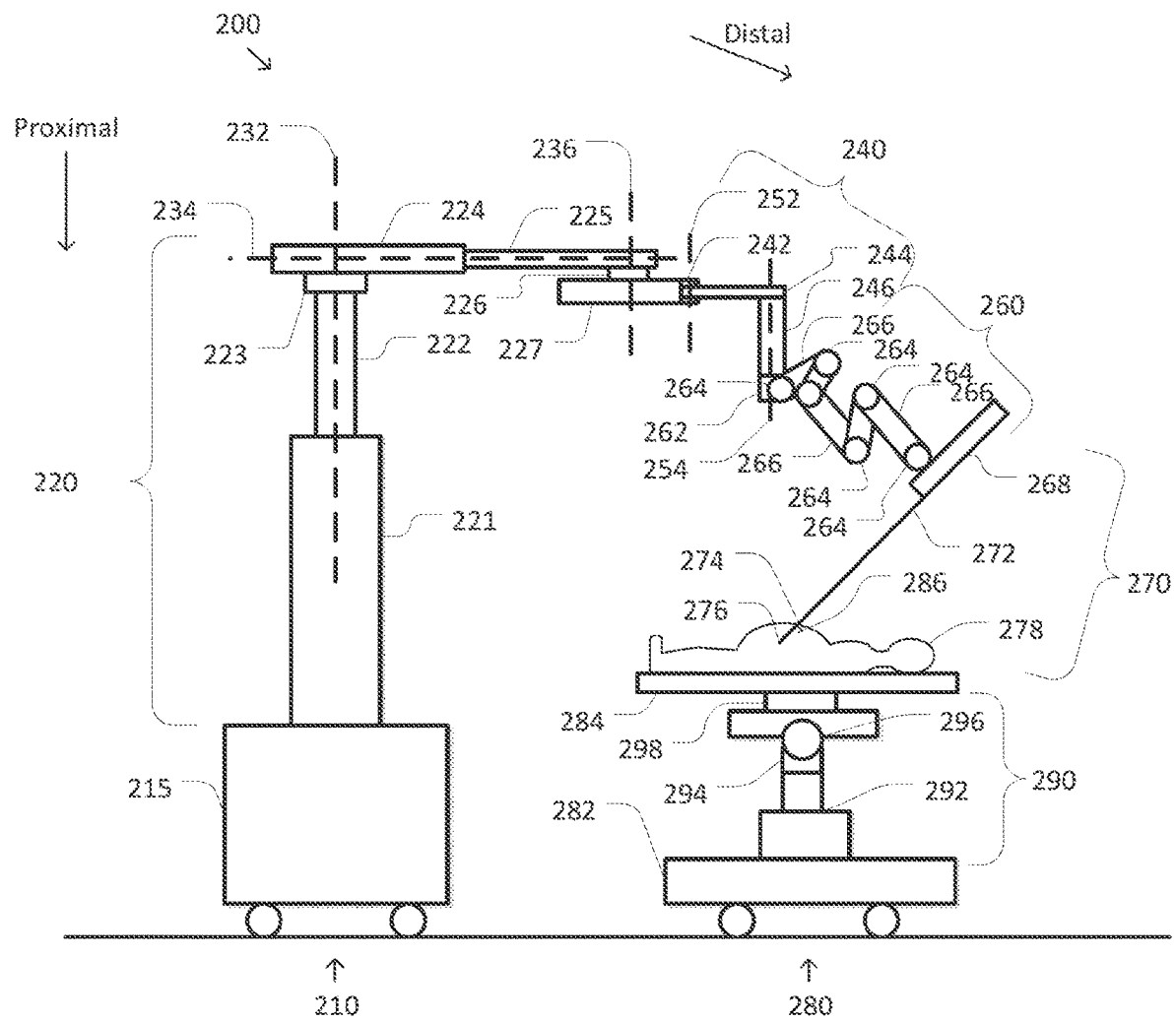
FIG. 2 is a simplified diagram showing a computer-assisted system according to some embodiments.

FIG. 2 is a simplified diagram showing a computer-assisted system 200 according to some embodiments. For example, the computer-assisted system 200 may be consistent with computer-assisted system 100. As shown in FIG. 2, the computer-assisted system 200 includes a computer-assisted device 210 with one or more articulated arms and a surgical table 280. Although not shown in FIG. 2, the computer-assisted device 210 and the surgical table 280 may be coupled together using one or more interfaces and one or more control units so that at least kinematic information about the surgical table 280 is known to the motion control application being used to perform motion of the articulated arms of the computer-assisted device 210.

The computer-assisted device 210 includes various links and joints. In the embodiments of FIG. 2, the computer-assisted device is generally divided into three different sets of links and joints. Starting at the proximal end with a mobile or patient-side cart 215 is a set-up structure 220. Coupled to a distal end of the set-up structure is a series of set-up joints 240. And coupled to a distal end of the set-up joints 240 is a manipulator 260, such as a universal surgical manipulator. In some examples, the series of set-up joints 240 and manipulator 260 may correspond to one of the articulated arms 120. And although the computer-assisted device is shown with only one series of set-up joints 240 and a corresponding manipulator 260, one of ordinary skill would understand that the computer-assisted device may include more than one series of set-up joints 240 and corresponding manipulators 260 so that the computer-assisted device is equipped with multiple articulated arms.

As shown, the computer-assisted device 210 is mounted on the mobile cart 215. The mobile cart 215 enables the computer-assisted device 210 to be transported from location to location, such as between operating rooms or within an operating room to better position the computer-assisted device in proximity to the surgical table 180. The set-up structure 220 is mounted on the mobile cart 215. As shown in FIG. 2, the set-up structure 220 includes a two part column including column links 221 and 222. Coupled to the upper or distal end of the column link 222 is a shoulder joint 223. Coupled to the shoulder joint 223 is a two-part boom including boom links 224 and 225. At the distal end of the boom link 225 is a wrist joint 226, and coupled to the wrist joint 226 is an orientation platform 227.

The links and joints of the set-up structure 220 include various degrees of freedom for changing the position and orientation (i.e., the pose) of the orientation platform 227. For example, the two-part column may be used to adjust a height of the orientation platform 227 by moving the shoulder joint 223 up and down along an axis 232. The orientation platform 227 may additionally be rotated about the mobile cart 215, the two-part column, and the axis 232 using the shoulder joint 223. The horizontal position of the orientation platform 227 may also be adjusted along an axis 234 using the two-part boom. And the orientation of the orientation platform 227 may also adjusted by rotation about an axis 236 using the wrist joint 226. Thus, subject to the motion limits of the links and joints in the set-up structure 220, the position of the orientation platform 227 may be adjusted vertically above the mobile cart 215 using the two-part column. The positions of the orientation platform 227 may also be adjusted radially and angularly about the mobile cart 215 using the two-part boom and the shoulder joint 223, respectively. And the angular orientation of the orientation platform 227 may also be changed using the wrist joint 226.

The orientation platform 227 may be used as a mounting point for one or more articulated arms. The ability to adjust the height, horizontal position, and orientation of the orientation platform 227 about the mobile cart 215 provides a flexible set-up structure for positioning and orienting the one or more articulated arms about a work space, such as a patient, located near the mobile cart 215. FIG. 2 shows a single articulated arm coupled to the orientation platform using a first set-up joint 242 (or "flex joint 242"). And although only one articulated arm is shown, one of ordinary skill would understand that multiple articulated arms may be coupled to the orientation platform 227 using additional first set-up joints.

The first set-up joint 242 forms the most proximal portion of the set-up joints 240 section of the articulated arm. The set-up joints 240 may further include a series of joints and links. As shown in FIG. 2, the set-up joints 240 include at least links 244 and 246 coupled via one or more joints (not expressly shown). The joints and links of the set-up joints 240 include the ability to rotate the set-up joints 240 relative to the orientation platform 227 about an axis 252 using the first set-up joint 242, adjust a radial or horizontal distance between the first set-up joint 242 and the link 246, adjust a height of a manipulator mount 262 at the distal end of link 246 relative to the orientation platform along an axis 254, and rotate the manipulator mount 262 about axis 254. In some examples, the set-up joints 240 may further include additional joints, links, and axes permitting additional degrees of freedom for altering a pose of the manipulator mount 262 relative to the orientation platform 227.

The manipulator 260 is coupled to the distal end of the set-up joints 240 via the manipulator mount 262. The manipulator 260 includes additional joints 264 and links 266 with an instrument carriage 268 mounted at the distal end of the manipulator 260. An instrument or manipulator tool 270 is mounted to the instrument carriage 268. The tool 270 includes a shaft 272, which is aligned along an insertion axis. The shaft 272 is typically aligned so that is passes through a remote center 274 associated with the manipulator 260. Location of the remote center 274 is typically maintained in a fixed translational relationship relative to the manipulator mount 262 so that operation of the joints 264 in the manipulator 260 result in rotations of the shaft 272 about the remote center 274. Depending upon the embodiment, the fixed translational relation of the remote center 274 relative to the manipulator mount 262 is maintained using physical constraints in the joints 264 and links 266 of the manipulator 260, using software constraints placed on the motions permitted for the joints 264, and/or a combination of both. In some examples, the remote center 274 may correspond to a location of a surgical port or incision site in a patient 278 after the manipulator 260 is docked with the patient 278. Because the remote center 274 corresponds to the surgical port, as the tool 270 is used, the remote center 274 remains stationary relative to the patient 278 to limit stresses on the anatomy of the patient 278 at the remote center 274. In some examples, the shaft 272 may be passed through a cannula (not shown) located at the surgical port.

At the distal end of the shaft 272 is a tool or tool tip 276. The degrees of freedom in the manipulator 260 due to the joints 264 and the links 266 may permit at least control of the roll, pitch, and yaw of the shaft 272 and/or the tool tip 276 relative to the manipulator mount 262. In some examples, the degrees of freedom in the manipulator 260 may further include the ability to advance and/or retreat the shaft 272 using the instrument carriage 268 so that the tool tip 276 may be advanced and/or retreated along the insertion axis and relative to the remote center 274. In some examples, the manipulator 260 may be consistent with a universal surgical manipulator for use with the da Vinci® Surgical System commercialized by Intuitive Surgical, Inc. of Sunnyvale, Calif. In some examples, the tool 270 may be an imaging device such as an endoscope, a gripper, a surgical tool such as a cautery or a scalpel, and/or the like. In some examples, the tool tip 276 may include additional degrees of freedom, such as roll, pitch, yaw, grip, and/or the like that allow for additional localized manipulation of portions of the tool tip 276 relative to the shaft 272.

During a surgery or other medical procedure, the patient 278 is typically located on the surgical table 280. The surgical table 280 includes a table base 282 and a table top 284 with the table base 282 being located in proximity to mobile cart 215 so that the tool 270 (also "instrument 270") and/or tool tip 276 may be manipulated by the computer-assisted device 210 while docked to the patient 278. The surgical table 280 further includes an articulated structure 290 that includes one or more joints or links between the table base 282 and the table top 284 so that the relative location of the table top 284, and thus the patient 278, relative to the table base 282 may be controlled. In some examples, the articulated structure 290 may be configured so that the table top 284 is controlled relative to a virtually-defined iso center 286 that may be located at a point above the table top 284. In some examples, iso center 286 may be located within the interior of the patient 278. In some examples, iso center 286 may be collocated with the body wall of the patient at or near one of the port sites, such as a port site corresponding to remote center 274.

As shown in FIG. 2, the articulated structure 290 includes a height adjustment joint 292 so that the table top 284 may be raised and/or lowered relative to the table base 282. The articulated structure 290 further includes joints and links to change both the tilt 294 and Trendelenburg 296 orientation of the table top 284 relative to the iso center 286. The tilt 294 allows the table top 284 to be tilted side-to-side so that either the right or left side of the patient 278 may be rotated upward relative to the other side of the patient 278 (i.e., about a longitudinal or head-to-toe axis of the table top 284). The Trendelenburg 296 allows the table top 284 to be rotated so that either the feet of the patient 278 are raised (Trendelenburg) or the head of the patient 278 is raised (reverse Trendelenburg). In some examples, either the tilt 294 and/or the Trendelenburg 296 rotations may be adjusted to generate rotations about iso center 286. The articulated structure 290 further includes additional links and joints 298 to slide the table top 284 back and forth relative to the table base 282 with generally a left and/or right motion as depicted in FIG. 2.

In many cases, it is desirable for an operator to manually position one or more joints, especially one or more non-actuated joints, of one or more articulated arms to obtain a predetermined configuration. In one illustrative example, an operator may desire to position the joints to obtain a packing configuration that facilitates packing and shipping of the device. For example, the packing configuration may minimize the space taken up by the articulated arms for efficient storage and/or maximize the space between arms to prevent them from colliding during handling. To avoid damage and/or delays during shipping, it is important for the operator to have the ability to reliably and efficiently set the joint positions into the packing configuration. However, it may be difficult for the operator to know when the correct configuration has been obtained when guiding the joints into position. Still further, the operator may not know which direction to move the joints to obtain the correct configuration when starting from an incorrect configuration. As a result, the operator may end up employing an inefficient and/or inaccurate approach for finding the correct configuration, such as an approach based on trial-and-error. The problem is particularly acute in a device such as computer-assisted device 210, as described previously with respect to FIG. 2, which may include four or more articulated arms, each arm further including four or more joints, such as set-up joints 240, each joint providing one or more degrees of freedom. In a device with many joints and many degrees of freedom, obtaining the correct packing configuration is a daunting, repetitive task with numerous opportunities for delays and/or errors.

A packing configuration is just one of many examples of useful predetermined configurations that an operator may wish to obtain by manually positioning one or more joints of a device. Another example is a calibration configuration, in which an operator positions the joints to allow calibration tests and/or measurements to be performed on one or more joints, articulated arms, and/or other parts of the device. Another example is a walk-through sequence, in which an operator steps through a predetermined sequence of configurations that may be used for testing, calibration and/or demonstration purposes. During a walk-through sequence, the ability to rapidly switch between the predetermined configurations is especially important to avoid tedious delays between each configuration of the sequence. Additional examples of predetermined configurations include set-up configurations used to prepare the device for surgical procedures, storage configurations used to prepare the device for long-term storage, and repair configurations used to provide access to hard-to-reach components to facilitate repairs.

In order to overcome the challenges associated with positioning one or more joints by hand, a feedback mechanism that helps guide the operator to the correct configuration is desirable. In some examples, the feedback mechanism helps inform the operator when the predetermined configuration has been obtained. In some examples, the feedback mechanism helps the operator in determining which direction to move a particular joint to reach the correct configuration. In some examples, the feedback mechanism helps prevent the operator from exceeding physical and/or practical constraints on the joint such as range of motion limits and/or velocity limits. When manually positioning a joint, the operator applies a force to move a joint either directly (e.g., by hand) or indirectly (e.g., by teleoperation). Therefore, haptic feedback, which provides the operator with a tactile response to the applied force, is a particularly convenient way of providing feedback to the operator, although other feedback mechanisms, such as visual and/or audio feedback, may be used in an analogous manner.

Figure 3:
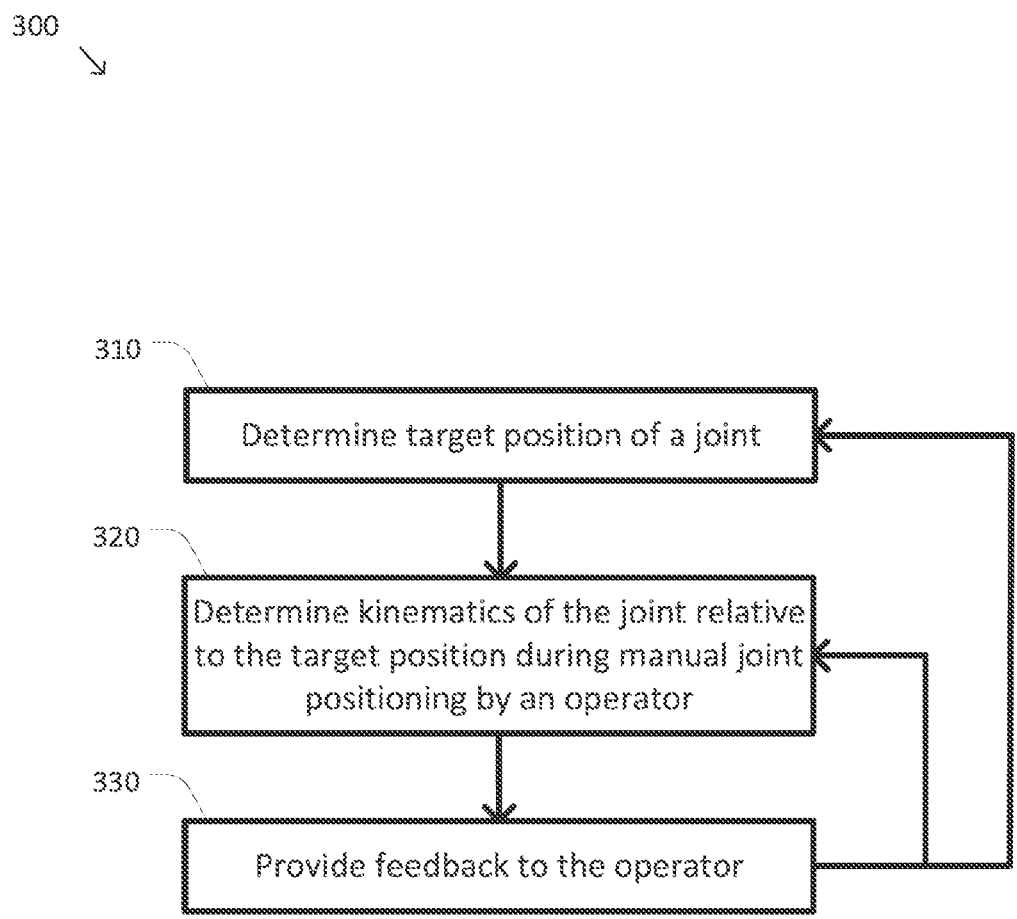
FIG. 3 is a simplified diagram of a method of providing feedback during manual joint positioning according to some embodiments.

FIG. 3 is a simplified diagram of a method 300 of providing feedback during manual joint positioning according to some embodiments. One or more of the processes 310-330 of method 300 may be implemented, at least in part, in the form of executable code stored on non-transient, tangible, machine readable media that when run by one or more processors (e.g., the processor 140 in control unit 130) may cause the one or more processors to perform one or more of the processes 310-330. In some embodiments, method 300 may be used to facilitate fast and accurate positioning of one or more joints of an articulated arm being guided by an operator. In some examples consistent with the embodiments of FIGS. 1 and 2, the articulated arm may correspond to articulated arm 120, and the joint may correspond to one of set-up joints 240 and/or joints 264 of manipulator 260. Without loss of generality, method 300 is described from the perspective of providing haptic feedback, although one of ordinary skill would understand that method 300 may be adapted to provide feedback using any suitable feedback mechanism.

According to some embodiments, method 300 may support one or more useful improvements over methods that do not provide feedback during manual joint positioning. In some examples, method 300 may facilitate rapid and accurate positioning of joints to obtain a desired configuration of one or more joints of one or more articulated arms. In some examples, method 300 may further reduce the likelihood of damage to an instrument and/or injury to a patient and/or operator due to erroneous calibration, testing, and/or positioning of joints.

At a process 310, a target position of the joint is determined. The target position is specified in units consistent with the type of joint being positioned. In some embodiments, such as when the joint is a prismatic joint, the target position may specify a distance representing a target extension of the joint. In some embodiments, such as when the joint is a rotational joint, the target position may specify an angle representing a target rotation of the joint. In some embodiments, the target position may specify a range of allowable positions. In some embodiments, such as when the joint is being positioned independently of other joints, the target position may be a fixed value. In some embodiments, such as when the joint is being positioned in conjunction with other joints, the target position may be a dynamic value that is determined based on a current configuration of one or more of the other joints. According to some embodiments, the target position may be selected from a predetermined sequence of target positions, such that each time a joint reaches a target position, the target position is updated to the next target position in the sequence. In some examples, such as when the joint is being positioned in conjunction with other joints, the target position may not be updated to the next target position in the sequence until one or more additional joints have reached respective target positions.

At a process 320, kinematics of the joint relative to the target position are determined during manual joint positioning by the operator. To manually position the joint, the operator applies a force to the joint (e.g., by direct hands-on manipulation of the joint and/or by teleoperation) that may be directed towards or away from the target position. In some embodiments, the force may be applied such that the operator has the ability to sense how the joint responds to the applied force (e.g., to differentiate between braked and unbraked joint motion). As the joint moves in response to the applied force, the kinematics of the joint are determined. The kinematics of the joint may be characterized by one or more parameters such as a current position, velocity, and/or acceleration of the joint (and/or corresponding angular parameters such as an angle, angular velocity, and/or angular acceleration) relative to the target position. According to some embodiments, the kinematic parameters may be determined using sensors associated with the joint, such as a position sensor, velocity sensor and/or an accelerometer. In some examples, the position sensor may be an encoder. In some examples, numerical integration and/or differentiation may be used to convert between positions, velocities, and/or accelerations. According to some embodiments, the kinematics may be determined relative to the target position and may specify, for example, whether the joint is currently at the target position, moving towards the target position, or moving away from the target position. An exemplary calculation illustrative of this embodiment proceeds as follows. The current joint position "y" is subtracted from the target joint position "r" to obtain an error value "e" representing an offset between the current and target joint position (i.e., e=r-y, with y, r, and e, having units of distance, angle, and/or the like). The velocity (and/or angular velocity) "v" of the joint is also recorded. When e is zero, the joint is determined to be at the target position. When e is positive and v is positive, or when e is negative and v is negative, then the joint is determined to be moving towards the target position. When e is positive and v is negative, or when e is negative and v is positive, then the joint is determined to be moving away from the target position with velocity v. When the target position includes a range of allowable positions, the error value e may be calculated for each allowable position r in the range, and the resulting e with the lowest absolute value may be used to determine the kinematics of the joint as described above.

Figure 4:
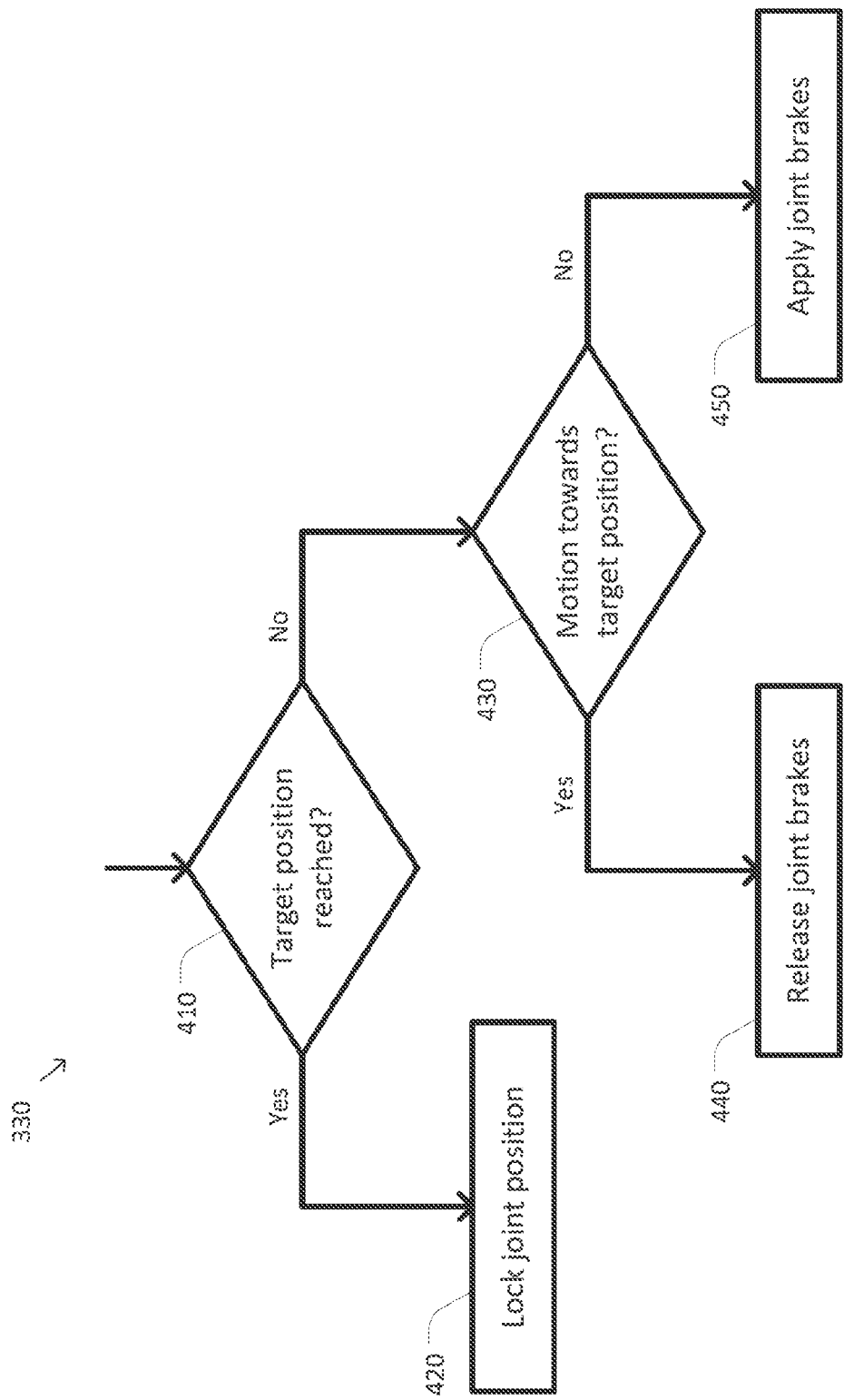
FIG. 4 is a simplified diagram of a method of providing feedback to an operator according to some embodiments.

At a process 330, feedback is provided to the operator. In some embodiments, the feedback may be haptic feedback applied to the joint using joint brakes, a vibratory motor, and/or the like. In some embodiments, the haptic feedback may be supplemented and/or supplanted with other stimuli such as visual feedback and/or audible feedback. In general, the feedback provides signals that elicit one or more desired responses from the operator, such as to stop moving the joint, to continue moving the joint, and/or to change the direction of the joint motion. The particular desired response at a given time depends upon the kinematics of the joint relative to the target position determined during process 320. FIG. 4 is a simplified diagram of a method for performing process 330 of providing feedback to the operator according to some embodiments in which feedback is provided using a haptic feedback signal applied using the joint brakes. In some examples, this method may be used to provide haptic feedback to the operator by applying the joint brakes based on the kinematics of the joint relative to the target position.

At a process 410, it is determined whether the joint is at the target position. According to some embodiments, the position of the joint may be determined using sensors associated with the joint, such as a position sensor, and compared with the target position to determine whether the joint is at the target position. When the joint is at the target position, the process 330 proceeds to a process 420 of locking the joint position. When the joint is not at the target position, the process 340 proceeds to a process 430 of determining whether the joint is moving towards the target position.

At a process 420, the joint position is locked. Process 420 is performed when the joint is determined to be at the target position. Accordingly, locking the joint position provides haptic feedback to the operator indicating that the target position has been obtained and the joint should not be moved further. In some embodiments, the joint position may be locked using the joint brakes, which may additionally, or alternately, be reinforced using another suitable joint locking mechanism, such as a locking pin and/or the like, to prevent further motion of the joint. Once the target position is obtained and the joint position is locked, process 330 is complete.

At a process 430, it is determined whether the joint is moving toward the target position. Process 430 is performed when the joint is not currently at the target position. Accordingly, the haptic feedback provided to the operator depends upon whether the joint is moving toward or away from the target position. According to some embodiments, the current joint position may be determined using sensors associated with the joint, such as a position sensor, and compared with the target joint position to determine whether the offset between the current joint position and the target joint position is positive or negative. In addition, the velocity of the joint may be determined using sensors associated with the joint, such as a velocity sensor, to determine whether the velocity of the joint is positive or negative. According to some embodiments, when the offset and the velocity both have the same sign, the joint is determined to be moving towards the target position, and when the offset and the joint velocity have opposite signs, the joint is determined to be moving away from the target position. When the joint is moving towards the target position, the process 340 proceeds to a process 440 of releasing the joint brakes. When the joint is moving away from the target position, the process 340 proceeds to a process 450 of applying the joint brakes.

At a process 440, the joint brakes are released. Process 440 is performed when the joint is moving toward the target position. Accordingly, releasing the brakes provides haptic feedback to the operator indicating that the joint is being moved correctly and should continue to move in the current direction. In some embodiments, when the brakes are released the joint may provide little resistance to the manual force applied by the operator. Once the joint brakes are released, process 330 completes and another cycle of method 300 is performed.

At a process 450, the joint brakes are applied. Process 450 is performed when the joint is moving away from the target position. Accordingly, applying the brakes provides haptic feedback to the operator indicating that the joint is being moved the wrong way and should be moved in the opposite direction. In some embodiments, the brake may be applied with a predetermined braking force. In some embodiments, the brake may be applied with a braking force that is proportional to the velocity of the joint away from the target position. Thus, as the operator moves the joint away from the target position with increasing velocity, the operator senses a greater amount of resistance from the joint brakes. In some embodiments, a proportional velocity gain factor, $k_v$, may be selected such that the braking force $F_b$ is proportional to the absolute value of the velocity away from the target position, $|v|$, according to the relationship $F_b = k_v |v|$.

In some examples, the joint brakes may be implemented using an electromagnetic power off brake and/or the like. The braking force applied by an electromagnetic power off brake is inversely proportional to an electrical signal (e.g., a current and/or voltage signal) and may exhibit hysteretic behavior. As a result of the hysteretic behavior, after the brake is released by applying a large electrical signal, the brake may respond unpredictably when attempting to reengage the brake unless a much lower electrical signal is subsequently applied to overcome the brake hysteresis. Accordingly, in some embodiments, appropriate constraints may be employed when releasing the brake during process 440 and/or applying the brake during process 450 to prevent the electrical signal to the brake from reaching threshold levels at which significant hysteretic behavior occurs.

Referring back to FIG. 3, once feedback is provided to the operator at process 330, the method 300 may return to process 320 to iteratively monitor the joint kinematics relative to the target position and provide additional feedback to the operator. In some embodiments, once the target position is reached, the method 300 may return to process 310 to set a new target position and begin a new iterative process of monitoring and feedback.

As discussed above and further emphasized here, FIGS. 3 and 4 are merely examples which should not unduly limit the scope of the claims. One of ordinary skill in the art would recognize many variations, alternatives, and modifications. According to some embodiments, the method 300 may be adapted to accommodate a joint having multiple separated target positions. For example, the method 300 may provide feedback that guides the operator to the nearest target position among the multiple target positions and/or may provide neutral feedback (i.e., feedback that does not depend on the direction the joint is moving in) when the joint is positioned between two target positions. According to some embodiments, the method 300 may provide feedback in order to maintain joint position, velocity and/or acceleration within allowable ranges associated with physical constraints of the joint. For example, during process 330, joint brakes may be applied when the joint position approaches a range of motion limit. Similarly, during process 330, joint brakes may be applied when the joint velocity and/or acceleration exceeds a predetermined threshold. According to some embodiments, the method 300 may employ techniques to mitigate sudden locking of the joint brakes at process 420, which may result in an undesirable jolt to the device when the joint is moving quickly. For example, feedback may be provided to the operator to indicate that the joint is close to and/or approaching the target position and should slow down and continue moving towards the target position to achieve a "soft" landing. In some examples, process 420 of locking the joint brakes may be disabled when the joint velocity exceeds a threshold velocity, such that the joint brakes do not lock while traveling at a fast velocity even when the joint reaches the target position.

Some examples of control units, such as control unit 130 may include non-transient, tangible, machine readable media that include executable code that when run by one or more processors (e.g., processor 140) may cause the one or more processors to perform the processes of method 300. Some common forms of machine readable media that may include the processes of method 300 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device comprising:
   an articulated structure comprising a joint; and
   a control unit coupled to the articulated structure;
   wherein, to provide feedback to a user during manual positioning of the joint by the user, the control unit is configured to:
      determine a first target position for the joint;
      release a brake associated with the joint when the joint is moving toward the first target position;
      apply the brake when the joint is moving away from the first target position; and
      change the first target position to a second target position when the joint is at the first target position.

2. The computer-assisted device of claim 1, wherein to determine whether the joint is moving toward the first target position, the control unit is configured to determine a velocity of the joint relative to the first target position.

3. The computer-assisted device of claim 1, wherein to apply the brake when the joint is moving away from the first target position, the control unit is configured to apply the brake with a braking force based on a velocity of the joint.

4. The computer-assisted device of claim 1, wherein the control unit is further configured to apply the brake to slow down the joint when the joint is close to the first target position.

5. The computer-assisted device of claim 1, wherein the control unit is further configured to provide feedback indicating that the joint should reverse direction when the joint is moving away from the first target position.

6. The computer-assisted device of claim 1, wherein after the first target position is changed to the second target position, the control unit is further configured to:

release the brake associated with the joint when the joint is moving toward the second target position; and apply the brake when the joint is moving away from the second target position.

7. The computer-assisted device of claim 1, wherein the first target position includes a range of allowable positions.

8. The computer-assisted device of claim 1, wherein the first target position is a fixed position.

9. The computer-assisted device of claim 1, wherein the first target position is a dynamic position determined based on kinematics of one or more other joints of the articulated structure.

10. The computer-assisted device of claim 1, wherein the first target position and the second target position are target positions in a sequence of predetermined configurations of the computer-assisted device.

11. A method of operating a computer-assisted device comprising a joint, the method comprising:

determining, by a control unit of the computer-assisted device, a first target position for the joint;

releasing, by the control unit, a brake associated with the joint when the joint is moving toward the first target position;

applying, by the control unit, the brake when the joint is moving away from the first target position; and changing, by the control unit, the first target position to a second target position when the joint is at the first target position.

12. The method of claim 11, wherein determining whether the joint is moving toward the first target position comprises determining a velocity of the joint relative to the first target position.

13. The method of claim 11, wherein applying the brake when the joint is moving away from the first target position comprises applying the brake with a braking force based on a velocity of the joint.

14. The method of claim 11, further comprising applying the brake to slow down the joint when the joint is close to the first target position.

15. The method of claim 11, further comprising providing feedback indicating that the joint should reverse direction when the joint is moving away from the first target position.

16. The method of claim 11, wherein:

the first target position includes a range of allowable positions; or the first target position is a fixed position; or the first target position is a dynamic position determined based on kinematics of one or more other joints of the computer-assisted device.

17. A non-transitory machine-readable medium comprising a plurality of machine-readable instructions which when executed by one or more processors associated with a computer-assisted medical device are adapted to cause the one or more processors to perform a method comprising:

determining a first target position for a joint;

releasing a brake associated with the joint when the joint is moving toward the first target position;

applying the brake when the joint is moving away from the first target position; and changing the first target position to a second target position when the joint is at the first target position.

18. The non-transitory machine-readable medium of claim 17, wherein applying the brake when the joint is moving away from the first target position comprises applying the brake with a braking force based on a velocity of the joint.

19. The non-transitory machine-readable medium of claim 17, further comprising applying the brake to slow down the joint when the joint is close to the first target position.

20. The non-transitory machine-readable medium of claim 17, further comprising providing feedback indicating that the joint should reverse direction when the joint is moving away from the first target position.

* * * * *

UNITED STATES PATENT AND TRADEMARK OFFICE
CERTIFICATE OF CORRECTION

PATENT NO. : 10,939,971 B2  
APPLICATION NO. : 16/934774  
DATED : March 9, 2021  
INVENTOR(S) : Paul G. Griffiths Page 1 of 1

It is certified that error appears in the above-identified patent and that said Letters Patent is hereby corrected as shown below:

On the Title Page

Item (63) Related U.S. Application Data:
Please delete "Continuation of application No. 15/558,525, filed as application No. PCT/US2016/022553 on Mar. 16, 2016, now Pat. No. 10,751,135." and insert --Continuation of application No. 15/558,525, filed on Sep. 14, 2017, now Pat. No. 10,751,135, which is a 371 of application No. PCT/US2016/022553, filed on Mar. 16, 2016.--.

Signed and Sealed this  
Twentieth Day of April, 2021

Drew Hirshfeld  
*Performing the Functions and Duties of the*  
*Under Secretary of Commerce for Intellectual Property and*  
*Director of the United States Patent and Trademark Office*